United States Patent [19]
Arakawa et al.

[11] Patent Number: 5,372,865
[45] Date of Patent: Dec. 13, 1994

[54] DOUBLE-SIDED PRESSURE-SENSITIVE ADHESIVE TAPE, LAMINATED STRUCTURE COMPRISING THE SAME, AND METHOD OF USE OF SAME

[75] Inventors: Masaaki Arakawa; Naomitu Tanaka; Teiji Sakashita, all of Osaka, Japan

[73] Assignee: Nitto Denko Corporation, Osaka, Japan

[21] Appl. No.: 927,666

[22] PCT Filed: Jan. 9, 1992

[86] PCT No.: PCT/JP92/00010

§ 371 Date: Sep. 9, 1992

§ 102(e) Date: Sep. 9, 1992

[87] PCT Pub. No.: WO92/12211

PCT Pub. Date: Jul. 23, 1992

[30] Foreign Application Priority Data

Jan. 9, 1991 [JP] Japan ................... 3-013006
Oct. 18, 1991 [JP] Japan ................... 3-271328
Dec. 26, 1991 [JP] Japan ................... 3-359235

[51] Int. Cl.[5] ......................................... C09J 7/02
[52] U.S. Cl. ................................. 428/40; 428/124; 428/194; 428/345; 428/349; 428/354; 428/355; 428/356; 428/447; 604/389; 604/390
[58] Field of Search ............... 428/40, 194, 354, 356, 428/355, 906, 352, 121, 124, 195, 220, 317.1, 317.3, 345, 349, 447; 427/208, 208.4, 208.6; 604/389, 390

[56] References Cited

FOREIGN PATENT DOCUMENTS 54-108833 8/1979 Japan .
61-94536 6/1986 Japan .

*Primary Examiner*—Ellis P. Robinson
*Assistant Examiner*—Nasser Ahmad
*Attorney, Agent, or Firm*—Sughrue, Mion, Zinn, Macpeak & Seas

[57] ABSTRACT

In the double-side pressure-sensitive tapes (A and B) of the first embodiment of the present invention, a first pressure-sensitive adhesive layer (2) comprising a blend of 100 parts by weight of an acrylic or rubber-based pressure-sensitive adhesive composition with from 0.01 to 30 parts by weight of a silicone polymer is formed on one side of a substrate and an acrylic or rubber-based pressure-sensitive adhesive layer is formed as a second pressure-sensitive adhesive layer (3) on the other side. By this, a double-side pressure-sensitive tape in which the pressure-sensitive adhesives, even when being bonded to each other, can thereafter be easily separated is obtained. For the pressure-sensitive tape of the second embodiment of the present invention, a second pressure-sensitive adhesive layer (54) is formed on one inner surface (53a) of both inner surfaces of a tape substrate (53) which are faced to each other and a first pressure-sensitive adhesive layer (55) is formed on the other inner surface (53b), with the second pressure-sensitive adhesive layer and the first pressure-sensitive adhesive layer being formed from pressure-sensitive adhesives having compositions different from each other so as to be separably bonded to each other, and a third pressure-sensitive adhesive layer (56) is formed on a suitable part of the tape substrate (53) other than the both faced surfaces. By this, it becomes possible to improve fixing strength without increasing the area of the tape substrate.

2 Claims, 6 Drawing Sheets

DOUBLE-SIDED PRESSURE-SENSITIVE ADHESIVE TAPE, LAMINATED STRUCTURE COMPRISING THE SAME, AND METHOD OF USE OF SAME

TECHNICAL FIELD

The first embodiment of the present invention relates to a double-side pressure-sensitive tape free from the necessity of a release paper, and to a double-side pressure-sensitive tape in which even if pressure-sensitive adhesives are bonded to each other, they can thereafter be easily separated. This tape is suitable for use in, for example, fixing absorbent articles such as paper diapers and napkins.

The second embodiment of the present invention relates to a pressure-sensitive tape for use, for example, as a fastener tape or the like for fixing the front part of a disposable diaper to the back part thereof.

BACKGROUND ART

As a double-side pressure-sensitive tape which does not use a release paper (separator), a tape obtained by coating a support on one side with an acrylic pressure-sensitive adhesive and on the other side with a rubber-based pressure-sensitive adhesive is known so far. However, this has drawbacks that adherends to which this tape is applicable are limited, that the property of separating pressure-sensitive adhesives from each other after laminating is unequivocally determined by the modulus of elasticity or the like of the pressure-sensitive adhesives and cannot be varied, and further that since acrylic pressure-sensitive adhesives, for example, have poor storage stability, they are unusable in articles to be used over a long period of time. Further, acrylic pressure-sensitive adhesives and rubber-based pressure-sensitive adhesives differ considerably from each other in properties such as adhesive force, heat resistance, and solvent resistance, and use of the rubber-based pressure-sensitive adhesive is unsuitable in case of bonding with the pressure-sensitive tape, followed by heat treatment, resin processing, or long-term use.

Also, a tape is known as a double-side pressure-sensitive tape free from the necessity of a release paper, which is obtained by coating a support on one side with a pressure-sensitive adhesive prepared by partially crosslinking an acrylic resin having a carboxyl group in a side chain with an isocyanate and on the other side with a pressure-sensitive adhesive prepared by partially crosslinking an acrylic resin having a hydroxyl group in a side chain with a melamine resin (e.g., Unexamined Published Japanese Patent Application 54-108833). However, this tape has a drawback that since the main components of the pressure-sensitive adhesives are limited to acrylic resins, adherends are limited naturally and adhesion to adherends such as polyolefins is poor. Further, use of this tape in sanitary articles or the like has been not preferable since there is a fear that formalin may be emitted because of the crosslinking with a melamine resin.

The first object of the present invention, which has been attained to solve those problems, is to provide a double-side pressure-sensitive tape which is free from the necessity of use of a release paper and which, even when those tapes are laminated with each other, can be easily separated at the interface between pressure-sensitive adhesive layers, by using a pressure-sensitive adhesive layer having a specific composition on one side thereof.

On the other hand, known as a pressure-sensitive tape for use as a fastener tape for fixing the front part of a disposable diaper to the back part thereof is, as shown, for example, in FIG. 20 and FIG. 21, a pressure-sensitive tape 10 produced by double-folding a tape substrate 11 in a manner such that a near-one-end part 11a and a near-other-end part 11b of the substrate become faced to each other, forming a first pressure-sensitive adhesive layer 12 on an inner surface of the near-one-end part 11a in the tape substrate 11, on the other hand, forming a release layer 13 for the first pressure-sensitive adhesive layer 12 on an inner surface of the near-other-end part 11b in the tape substrate 11, and further forming a second pressure-sensitive adhesive layer 14 on an outer surface of the near-other-end part 11b in the tape substrate 11 (Unexamined Published Japanese Utility Model Application 61-94536).

That is, this pressure-sensitive tape 10 has been designed to be used in a manner such that the pressure-sensitive tape 10 is applied beforehand through the second pressure-sensitive adhesive layer 14 to the inner surface of a back part 5A1 in a diaper 5A, the diaper 5A is applied to a baby or infant, the near-one-end part 11a of the tape substrate 11 is peeled from the near-other-end part 11b, and this near-one-end part 11a is bonded to a center tape 5A3 disposed on a front part 5A2 of the diaper 5A, thereby fixing the back part 5A1 of the diaper 5A to the front part 5A2.

According to this pressure-sensitive tape, there is no need to separately dispose a release tape because the tape substrate 11 itself functions as a release tape for the first pressure-sensitive adhesive layer 12 and protects the first pressure-sensitive adhesive layer 12. The above pressure-sensitive tape, therefore, has an advantage that the production process can be simplified and the cost can be reduced.

However, in this pressure-sensitive tape 10, since the inner surface of the near-one-end part 11a in the tape substrate 11 is the only part where the first pressure-sensitive adhesive layer 12 can be formed, the area in which the tape substrate 11 is bonded to the center tape 5A3 is small. Because of this, there has been a problem that the fixing strength to the front part 5A2 of the diaper 5A is so low that the tape substrate 11 shifts as shown by the alternate long and short dash line in FIG. 22 if a tensile force is applied, according to the movement of the baby or infant wearing the diaper 5A, to the tape substrate 11 in a direction along the length of the substrate, and this not only loosens the diaper 5A but also is prone to cause rubefaction or a rash on the skin 5B of the baby or infant because the other end part in the tape substrate 11 contacts with the skin 5B of the baby or infant.

Although it is thought that the above problem may be solved by increasing the area of the first pressure-sensitive adhesive layer 12 by elongating the length size of the tape substrate 11, this results in an increase in the amount of a material used for producing the tape substrate 11 and, as a result, the effect of cost reduction brought about by unnecessity of a release paper is lost.

The second object of the present invention is to provide a pressure-sensitive tape which can markedly improve a fixing strength without increasing the area of the tape substrate.

DISCLOSURE OF THE INVENTION

Accordingly, the first embodiment of the present invention provides a double-side pressure-sensitive tape comprising a first pressure-sensitive adhesive layer formed on one side of a substrate and made of a blend of 100 parts by weight of an acrylic or rubber-based pressure-sensitive adhesive composition with from 0.01 to 30 parts by weight of a silicone polymer, and an acrylic or rubber-based pressure-sensitive adhesive layer as a second pressure-sensitive adhesive layer formed on the other side.

The second embodiment of the present invention further provides a pressure-sensitive tape in which one tape substrate is double-folded, a second pressure-sensitive adhesive layer is formed on one of both faced surfaces of the tape substrate and a first pressure-sensitive adhesive layer is formed on the other surface, with the second pressure-sensitive adhesive layer and first pressure-sensitive adhesive layer being made of pressure-sensitive adhesives having compositions different from each other so as to be separably bonded to each other, and a third pressure-sensitive adhesive layer is formed on a suitable part of the tape substrate other than the both faced surfaces.

BRIEF DESCRIPTION OF THE DRAWINGS

FIG. 13 is used.

Description of the Symbols

Figure 1:
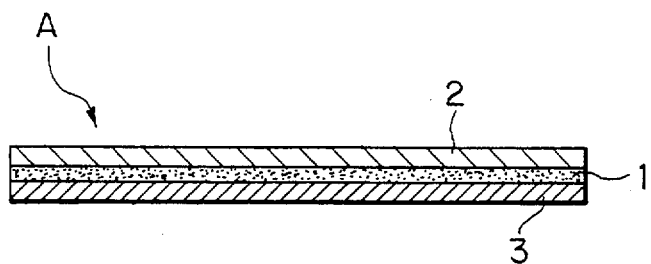
FIG. 1 is a sectional view showing one example of the double-side pressure-sensitive tape of the present invention.

1 Substrate
2 First pressure-sensitive adhesive layer
3 Second pressure-sensitive adhesive layer
A Double-side pressure-sensitive tape
B Double-side pressure-sensitive tape
4 Paper diaper
C Pressure-sensitive tape
5 Pressure-sensitive adhesive layer
6 Napkin
7 Package sack
8 Dry edge part
51 Pressure-sensitive tape
52 Roll of pressure-sensitive tape
53 Tape substrate
54 Second pressure-sensitive adhesive layer
55 First pressure-sensitive adhesive layer
56 Third pressure-sensitive adhesive layer
5A Diaper

BEST MODES FOR CARRYING OUT THE INVENTION

The first embodiment of the present invention is first explained below according to the drawings of examples.

In FIG. 1, which is a sectional view showing one example of a double-side pressure-sensitive tape A of the present invention, a first pressure-sensitive adhesive layer 2 is formed on one side of a substrate 1 and a second pressure-sensitive adhesive layer 3 on the other side.

Here the first pressure-sensitive adhesive layer is a pressure-sensitive adhesive layer made of a blend of 100 parts by weight of an acrylic or rubber-based pressure-sensitive adhesive composition with from 0.01 to 30 parts by weight of a silicone polymer.

The acrylic polymer constituting the acrylic pressure-sensitive adhesive composition which is the major constituent component of the first pressure-sensitive adhesive layer is not particularly limited and a conventionally known one can be applied as is. Ones produced by copolymerizing one or two of alkyl esters of acrylic acid and alkyl esters of methacrylic acid with the carbon atom numbers in the alkyl group being from 2 to 14, as the major monomer contained in an amount of at least 50% by weight, with a functional group-containing monomer such as an unsaturated carboxylic acid copolymerizable with the above esters and a modifying monomer such as styrene, vinyl acetate, or acrylonitrile, as the remainder, can generally be mentioned. One of or a mixture of two or more of these can suitably be selected and used.

Further, the rubber-based polymer constituting the rubber-based pressure-sensitive adhesive composition also is not particularly limited, and natural rubber, styrene-isoprene-styrene block copolymers, styrene-butadiene-styrene copolymers, styrene-ethylene-butadiene-styrene copolymers, and the like can be mentioned. One of or a mixture of two or more of these can suitably be selected and used.

As the silicone polymer to be blended with the above major component, polydimethylsiloxane, polyorganosiloxanes, and mixtures-modification products thereof can be mentioned, and it usually contains a silicone oil as a major component. A silicone resin can suitably be added as a release control agent.

The blended amount of such silicone polymer is from 0.01 to 30 parts by weight, preferably from 0.5 to 10 parts by weight, per 100 parts by weight of the above-described acrylic or rubber-based pressure-sensitive adhesive composition. In the case of being below 0.01 part by weight, the effect of separating from the second pressure-sensitive adhesive layer described later is not obtained, while amounts exceeding 30 parts by weight are not preferred in adhesion and holding properties.

It is presumed that this is because due to the incorporation of such silicone polymer, the silicone bleeds to the surface of the pressure-sensitive adhesive layer with the lapse of date to form a silicone film. Such silicone film has adhesive force because it has viscoelasticity.

The second pressure-sensitive adhesive layer in the present invention is not particularly limited, and the above-described acrylic or rubber-based pressure-sensitive adhesive composition which is an ordinary pressure-sensitive adhesive can be used.

Figure 2:
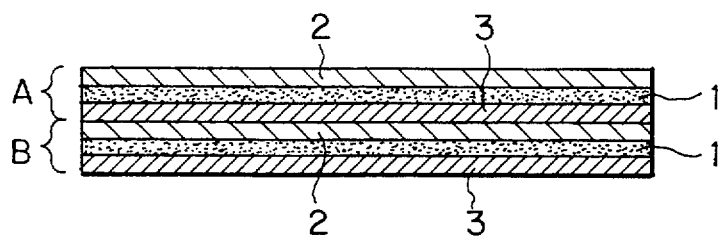
FIG. 2 is a sectional view showing another example of the double-side pressure-sensitive tape of the present invention.

FIG. 2 is a sectional view showing another example of the double-side pressure-sensitive tape of the present invention, and it is a composite double-side pressure-sensitive tape obtained by laminating two double-side pressure-sensitive tapes of FIG. 1. Here the second pressure-sensitive adhesive layer 3 of the double-side pressure-sensitive tape A and the first pressure-sensitive adhesive layer 2 of the other double-side pressure-sensitive tape B are laminated with both layers facing in a manner such that both layers are separable at their interface. Here, of course, not only the same tapes are laminated, but also two or more double-side pressure-sensitive tapes different from each other in the composition of pressure-sensitive adhesive can be laminated to form a composite double-side pressure-sensitive tape.

Figure 3:
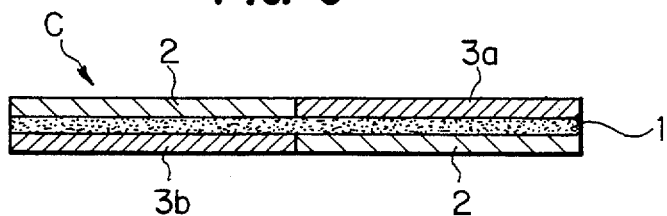
FIG. 3 is a sectional view showing another example of the double-side pressure-sensitive tape of the present invention.

In FIG. 3, which is a sectional view showing another example of the double-side pressure-sensitive tape of the present invention, a first pressure-sensitive adhesive layer 2 is formed in one side part on one side of a substrate 1 and a second pressure-sensitive adhesive layer 3a is formed on the remaining part on the same side, and a second pressure-sensitive adhesive layer 3b and a first pressure-sensitive adhesive layer 2 are formed on the other side in its parts corresponding to the layers 2 and 3a, respectively.

Figure 4:
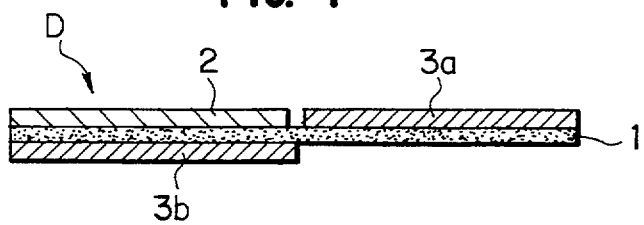
FIG. 4 is a sectional view showing another example of the double-side pressure-sensitive tape of the present invention.

In FIG. 4, which is a sectional view showing another example of the double-side pressure-sensitive tape of the present invention, a first pressure-sensitive adhesive layer 2 is formed in one side part on one side of a substrate 1, a second pressure-sensitive adhesive layer 3a is formed in the remaining part on the same side, and a second pressure-sensitive adhesive layer 3b is formed on the other side in its part facing to the first pressure-sensitive adhesive layer 2.

Further, in the double-side pressure-sensitive tapes shown in FIG. 3 and FIG. 4, the second pressure-sensitive adhesive layers 3a and 3b may be pressure-sensitive adhesives whose compositions are either identical or different.

Figure 5:
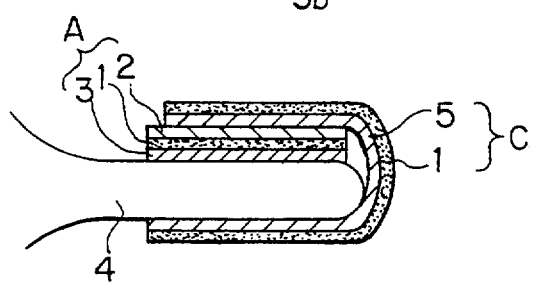
FIG. 5 is an illustrative view showing an example in which a double-side pressure-sensitive tape of the present invention is used in a fastener part of a paper diaper.
Figure 6:
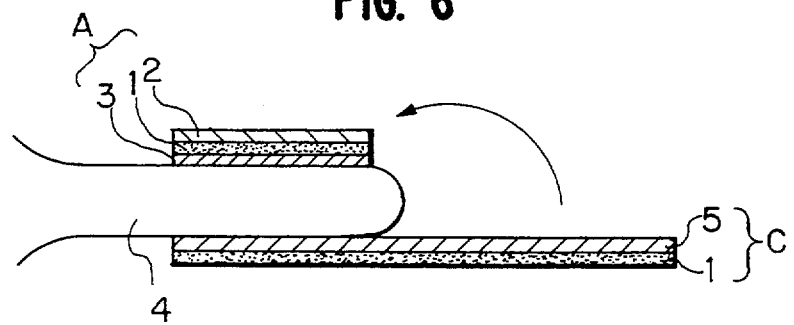
FIG. 6 is an illustrative view showing an example in which a double-side pressure-sensitive tape of the present invention is used in a fastener part of a paper diaper.

FIG. 5 and FIG. 6 are illustrative views showing examples in which the double-side pressure-sensitive tape A of FIG. 2 is used as a release tape of a paper diaper. For example, the second pressure-sensitive adhesive layer 3 of the double-side pressure-sensitive tape A is bonded and fixed to the inner surface of the back part of a paper diaper 4 and an ordinary pressure-sensitive tape C is bonded and fixed as a fastener tape to the outer surface, so that before use, the pressure-sensitive adhesive layer 5 of this pressure-sensitive tape and the first pressure-sensitive adhesive layer 2 of the double-side pressure-sensitive tape A are bonded to each other in a state such that the two layers are separable at their interface, as shown in FIG. 5. When the release tape is used, the pressure-sensitive tape C is peeled at the interface between pressure-sensitive adhesive layers as shown in FIG. 6 and is bonded and fixed to the front part of the paper diaper 4, whereby the diaper can be put on.

Figure 7:
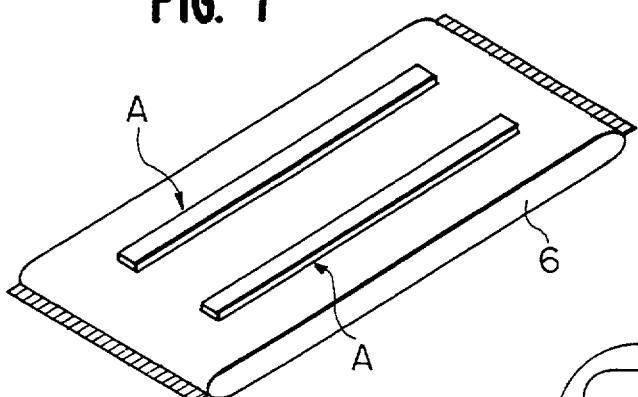
FIG. 7 is an illustrative view showing an example in which a double-side pressure-sensitive tape of the present invention is used in a napkin.
Figure 8:
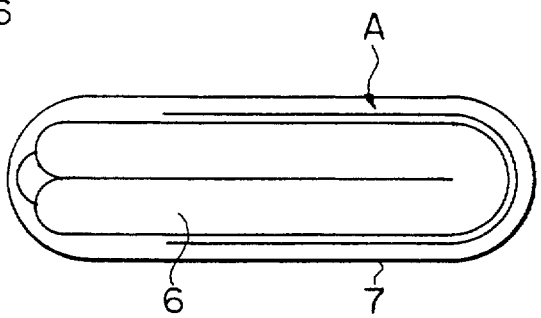
FIG. 8 is an illustrative view showing an example in which the napkin shown in FIG. 7 has been packaged in a package sack.

FIG. 7 is an illustrative view showing an example in which the double-side pressure-sensitive tape A of FIG. 1 is disposed on the back side of a napkin 6. As shown in FIG. 8, it can be folded and packaged in a plastic sack 7 such as polyethylene.

Figure 9:
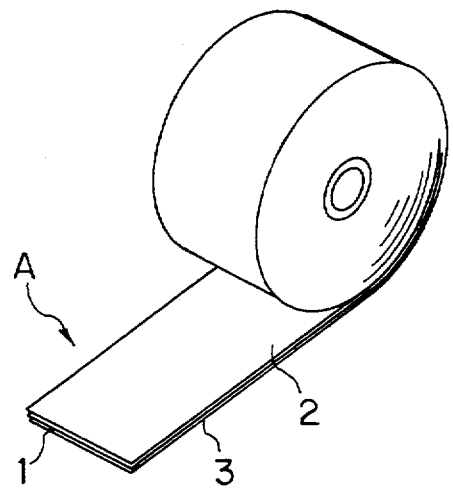
FIG. 9 is an illustrative view showing a double-side pressure-sensitive tape of the present invention which has been wound and is in a rolled state.

FIG. 9 is an illustrative view showing a double-side pressure-sensitive tape A of the present invention which has been wound and is in a rolled state. Since a first pressure-sensitive adhesive layer 2 and a second pressure-sensitive adhesive layer 3 have different compositions, the two pressure-sensitive adhesive layers can be easily separated at their interface and, hence, no release paper is needed.

Figure 10:
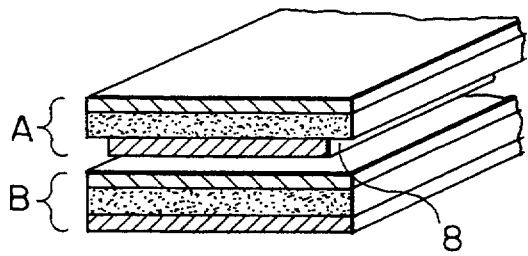
FIG. 10 is an illustrative view showing another example of the double-side pressure-sensitive tape of the present invention.
Figure 11:
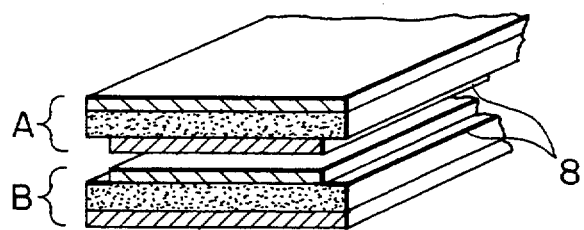
FIG. 11 is an illustrative view showing another example of the double-side pressure-sensitive tape of the present invention.

Further, in the present invention, separation of pressure-sensitive adhesive layers at their interface can be rendered easier by making edge parts of a substrate 1 so-called dry edge parts 8 in which at least one of the faced pressure-sensitive adhesive layers is omitted as shown in FIG. 10 and FIG. 11.

EXAMPLE 1

One part by weight of an addition-type silicone polymer (polydimethylsiloxane containing 10% by weight of a polyorganosiloxane) was added to 100 parts by weight of an acrylic pressure-sensitive adhesive obtained by copolymerizing butyl acrylate and acrylic acid (weight ratio=97:3), 0.02 part by weight of a platinum catalyst was added, and the mixture was heated at 130° C. for 60 seconds, thereby obtaining a first pressure-sensitive adhesive composition.

This first pressure-sensitive adhesive composition was coated on one side of a 25 μm-thick polyethylene terephthalate film, the other side was coated with as a second pressure-sensitive adhesive an acrylic pressure-sensitive adhesive containing polybutyl acrylate as a major component, and the film was dried, thereby obtaining a double-side pressure-sensitive tape of the present invention.

The double-side pressure-sensitive tape obtained was wound into a roll as shown in FIG. 9, and unwinding was then conducted. As a result, the tape was able to be unwound smoothly even without a release paper, posing no practical problem.

EXAMPLE 2

Five parts by weight of an addition-type silicone polymer (polydimethylsiloxane) was added to 100 parts by weight of a rubber-based, SIS pressure-sensitive adhesive containing as a major component a styrene-isoprene-styrene block copolymer having a styrene content of 14% by weight, 0.3% by weight of a platinum catalyst was added, and the mixture was heated at 130° C. for 60 seconds, thereby obtaining a first pressure-sensitive adhesive composition.

This first pressure-sensitive adhesive composition was coated on one side part on one side of a 150 μm-thick polyethylene film, two one side parts on both sides were coated with as a second pressure-sensitive adhesive a rubber-based pressure-sensitive adhesive comprising a styrene-ethylene-butadiene-styrene block copolymer, and drying was conducted, thereby obtaining a double-side pressure-sensitive tape of the present invention.

The thus-obtained double-side pressure-sensitive tape was applied to a fastener part of a paper diaper as shown in FIG. 6 and the diaper was subjected to a use test by 10 persons. As a result, an answer was received from all to the effect that the diaper had fit in well with the skin and been free from unfastening and urine leakage had become less.

Next, the second embodiment of the present invention is then explained below.

The second embodiment of the present invention relates to a pressure-sensitive tape in which one tape substrate is double-folded, a second pressure-sensitive adhesive layer is formed on one of both faced surfaces of the tape substrate and a first pressure-sensitive adhesive layer is formed on the other surface, with the second pressure-sensitive adhesive layer and first pressure-sensitive adhesive layer being made of pressure-sensitive adhesives having compositions different from each other so as to be separably bonded to each other, and a third pressure-sensitive adhesive layer is formed on a suitable part of the tape substrate other than the both opposed surfaces.

Due to such a construction, two members can be fixed by pressing the third pressure-sensitive adhesive layer against one member to bond the tape substrate to the member, separating the second pressure-sensitive adhesive layer from the first pressure-sensitive adhesive layer while keeping the bonded state as is, thereby to unfold the folded tape substrate to make it in the shape of a single sheet, and pressing the second pressure-sensitive adhesive layer and first pressure-sensitive adhesive layer exposed by the unfolding, against the other member to bond the tape substrate to the other member.

Next, examples of the second embodiment of the present invention are explained based on drawings (FIG. 12 to FIG. 20).

Figure 12:
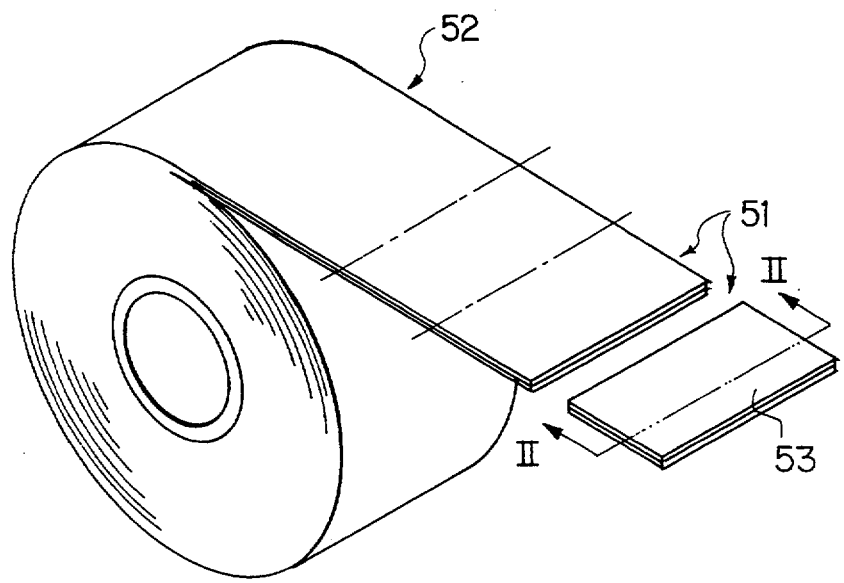
FIG. 12 is a perspective view of a pressure-sensitive tape of the present invention and a roll thereof.

In FIG. 12, symbol 51 denotes a pressure-sensitive tape, and the pressure-sensitive tape 51 is produced by unwinding a roll 52 obtained by winding a continuous tape material into a roll, to make the tape material straight, and cutting it to a certain size.

Figure 13:
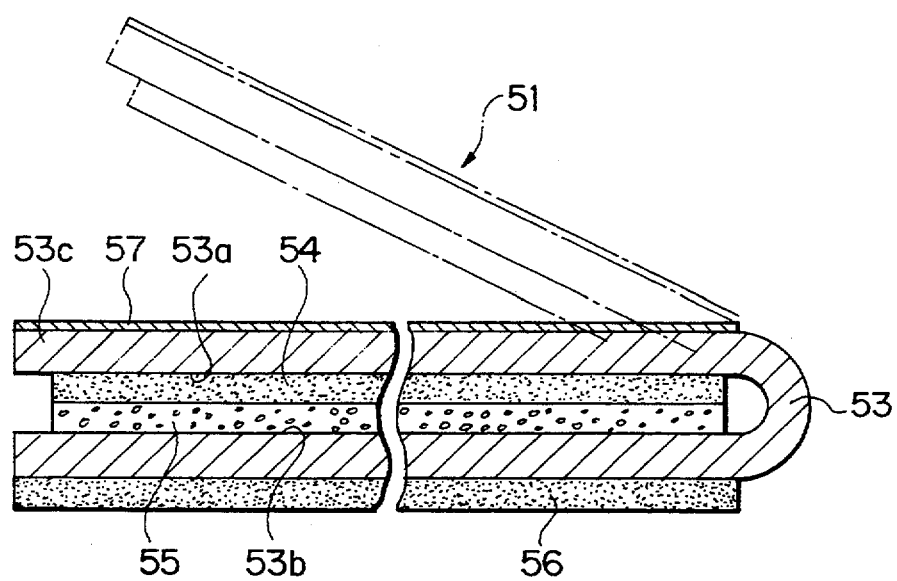
FIG. 13 is an enlarged sectional view taken on II—II of FIG. 12.

The above pressure-sensitive tape 51 has a tape substrate 53 of a rectangular shape made of a sheet material such as a synthetic resin film such as polypropylene film or the like, paper, cloth, or the like. As shown in FIG. 13, this tape substrate 53 is double-folded around the middle part along the longitudinal direction so that the near-one-end part and near-other-end part along the longitudinal direction come to overlie each other almost completely, and a second pressure-sensitive adhesive layer 54 is formed on one surface 53a of both faced surfaces 53a and 53b and a first pressure-sensitive adhesive layer 55 is formed on the other surface 53b.

In doing so, both pressure-sensitive adhesive layers 55 and 54 are made to have different compositions, that is, for example, the second pressure-sensitive adhesive layer 54 is formed from a pressure-sensitive adhesive composition obtained by blending 50 parts by weight of an SIS block copolymer with 50 parts by weight of a petroleum resin, while the first pressure-sensitive adhesive layer 55 is formed from a pressure-sensitive adhesive composition obtained by blending 98 parts by weight of an acrylic pressure-sensitive adhesive composition with 2 parts by weight of an addition-type silicone, whereby the second pressure-sensitive adhesive layer 4 and the first pressure-sensitive adhesive layer 55 can be bonded to a state such that they are separable as shown by the alternate long and short dash lines in FIG. 13.

Further, on the outer surface of the near-other-end part in the tape substrate 53, a third pressure-sensitive adhesive layer 56 is formed by coating a pressure-sensitive adhesive having the same composition as the second pressure-sensitive adhesive layer 54, while on the outer surface of the near-one-end part in the tape substrate 53, a release layer 57 for the third pressure-sensitive adhesive layer 56 is formed so as to enable the pressure-sensitive tape to be unwound after being wound into a roll 52.

Incidentally, at one end of the tape substrate 53, a pinch part 53c uncoated with the second pressure-sensitive adhesive layer 54 has been formed in order to provide a handhold for peeling.

Figure 14:
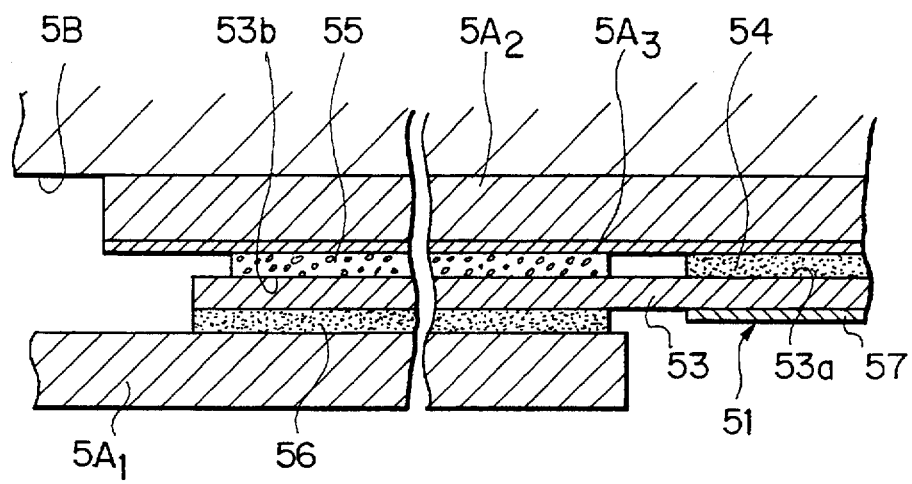
FIG. 14 is a sectional view taken on III—III of FIG. 20 in which the pressure-sensitive tape of FIG. 12
Figure 20:
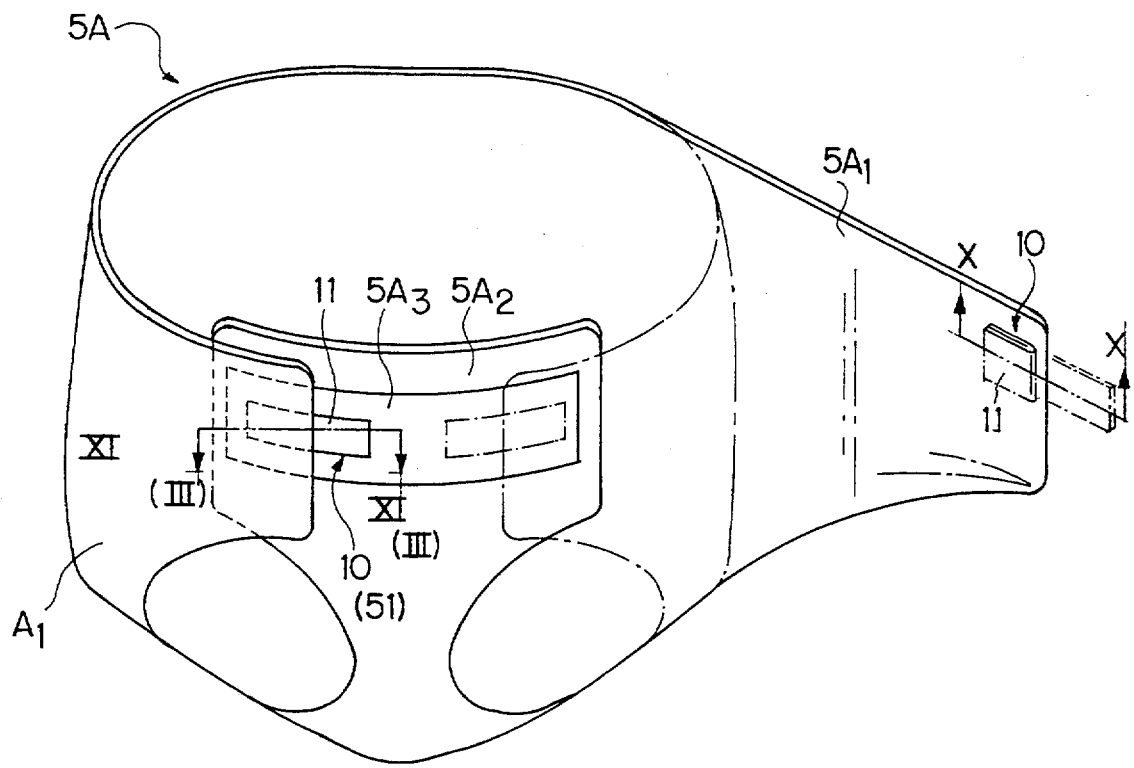
FIG. 20 is a perspective view of a diaper.
Figure 21:
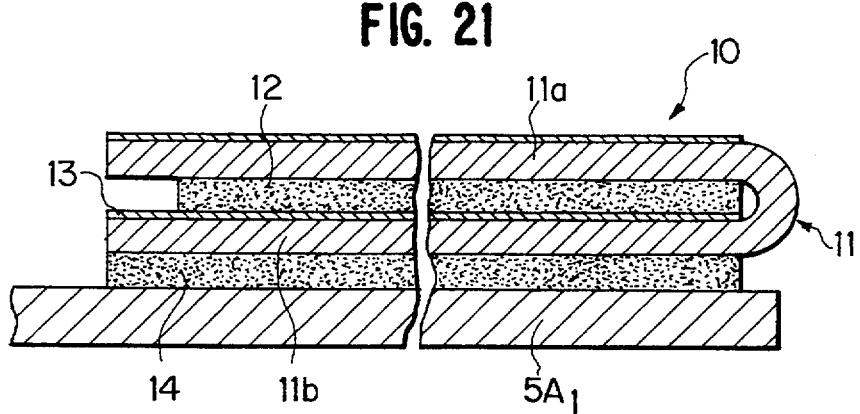
FIG. 21 is a sectional view taken on X—X of FIG. 20.
Figure 22:
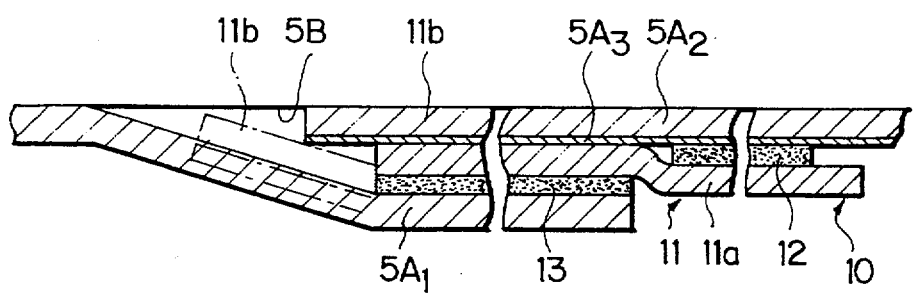
FIG. 22 is a sectional view taken on XI—XI of FIG. 20.

As shown in FIG. 20 and FIG. 14, the pressure-sensitive tape 51 having such construction is used as a fastener tape in a diaper 5A to fix a back part 5A1 of the diaper 5A to a front part 5A2, whereby the tape substrate 53 is bonded to the front part 5A2 through the second pressure-sensitive adhesive layer 54. Further, it is bonded to the front part 5A2 also by the first pressure-sensitive adhesive layer 55, and the area in which the tape substrate 53 is bonded to a center tape 5A3 on the front part 5A2 in the diaper 5A can be doubled as compared with conventional ones. Therefore, shifting the tape substrate 53 along the surface of the center tape 5A3 can be surely prevented, and the disadvantages that the diaper 5A becomes loose due to the movement of the infant or baby or the other end part of the tape substrate 53 appears from the side edge of the front part 5A2 to come into contact with the skin 5B of the infant or baby can be surely prevented.

The present inventors compared the shear adhesive strength of a practical sample of the second embodiment of the present invention with that of a prior art sample by the following method.

That is, for the practical sample of the present application, a tape substrate 53 having a width of 25 mm and a length of 40 mm was formed from a non-stretched polypropylene film having a thickness of 100 μm, and a second pressure-sensitive adhesive layer 54 was formed from a pressure-sensitive adhesive prepared by blending 50 parts by weight of a styrene-isoprene-styrene block copolymer having a styrene content of 14% by weight with 50 parts by weight of a petroleum resin, at a thickness of 50 μm and at a length of 10 mm along the direction of the length of the tape substrate 53. On the other hand, a first pressure-sensitive adhesive layer 55 was formed from a pressure-sensitive adhesive prepared by blending 98 parts by weight of an acrylic pressure-sensitive adhesive such as polybutyl acrylate with 2 parts by weight of an addition-type silicone such as a dimethylpolysiloxane containing 10 parts by weight of a three-dimensional organopolysiloxane at a thickness of 50 μm and at a length of 20 mm along the direction of the length of the tape substrate 53.

On the other hand, the comparative sample was made to have the same structure as the practical sample of the present application except only that the first pressure-sensitive adhesive layer 55 in the present application had not been formed.

Then, in a standard atmosphere of 23° C. and a humidity of 65%, these samples were superposed on an adherend prepared by coating the surface of a stretched polypropylene film having a thickness of 25 μm with a release agent having a long-chain alkyl group at a thickness of 0.1 mm in a manner such that the second pressure-sensitive adhesive layers 54 faced downward, and the samples were press-bonded by moving a 2 Kg roller forward and backward once at a speed of 50 mm/sec. After the samples were allowed to stand for 30 seconds, the tape substrates 53 were pulled at a speed of 300 mm/min in one direction along the direction of the substrate length, and the maximum loads at the time when the pressure-sensitive tapes 51 were peeled off the adherend were read.

As a result, the maximum load required for peeling the practical sample of the present invention was 6.0 Kg on average, whereas that for the prior art sample was 3.9 Kg on average, demonstrating that the embodiment sample of the present application had a higher peel strength.

Incidentally, in the case where a pressure-sensitive adhesive containing a silicone is used as the first pressure-sensitive adhesive layer 55, the adhesive strength of the second pressure-sensitive adhesive layer 54 did never increase with the lapse of date and the separability of the second pressure-sensitive adhesive layer 54 from the first pressure-sensitive adhesive layer 55 did never decrease with the lapse of date, although it is presumed that the above is because the silicone contained in the pressure-sensitive adhesive bleeds to the pressure-sensitive adhesive layer surface with the lapse of date. In this case, it is preferable to add from 0.01 to 30 parts by weight of a silicone polymer to 100 parts by weight of an acrylic or rubber-based pressure-sensitive adhesive composition. If the amount of the silicone polymer added is smaller than this range, separation from the second pressure-sensitive adhesive layer 54 becomes difficult, while if the amount of the silicone polymer added is larger than that, the adhesive strength decreases.

FIG. 15 to FIG. 19 show other embodiments of the present invention.

Figure 15:
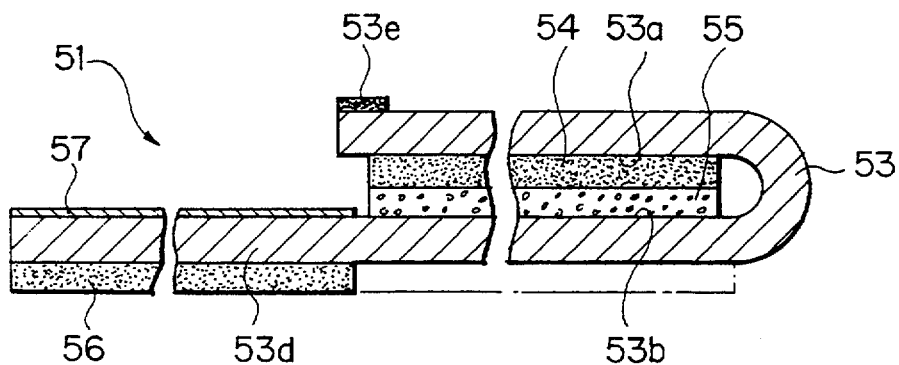
FIG. 15 is a view showing another embodiment of the pressure-sensitive tape of the present invention.

In FIG. 15 is shown one obtained by partly folding a tape substrate 53 in a manner such that surfaces 53a and 53b of a near-one-end part in the substrate come to face to each other, forming a second pressure-sensitive adhesive layer 54 and a first pressure-sensitive adhesive layer 55 on both faced surfaces 53a and 53b, and forming a third pressure-sensitive adhesive layer 56 on a surface which is one of both surfaces of a tape substrate 53's part 53d not overlying or underlying other part and which is on the side opposite to the second and first pressure-sensitive adhesive layers 54 and 55. Symbol 53e is a colored part for rendering a pinch part visible and recognizable.

In the case of this FIG. 15, the third pressure-sensitive adhesive layer 56 may be extended to near the central part around which the tape substrate 53 has been folded, as shown by the alternate long and short dash line.

Figure 16:
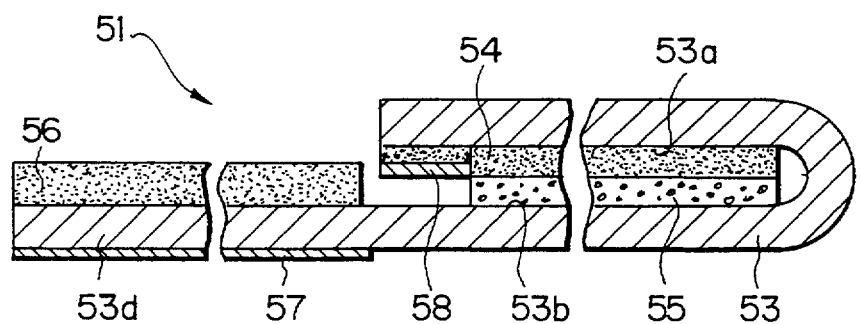
FIG. 16 is a view showing a modification example of FIG. 15.

In FIG. 16 is shown a modification example of the above-described FIG. 15, i.e., one in which a third pressure-sensitive adhesive layer 56 is formed on a surface which is one of both surfaces of the tape substrate 53's part 53d not overlying or underlying other part and which is on the side same as that where the second and first pressure-sensitive adhesive layers 55 and 54 are formed, and further a tape piece 58 for pinching is bonded to an inner surface of one end part in the tape substrate 53.

Figure 17:
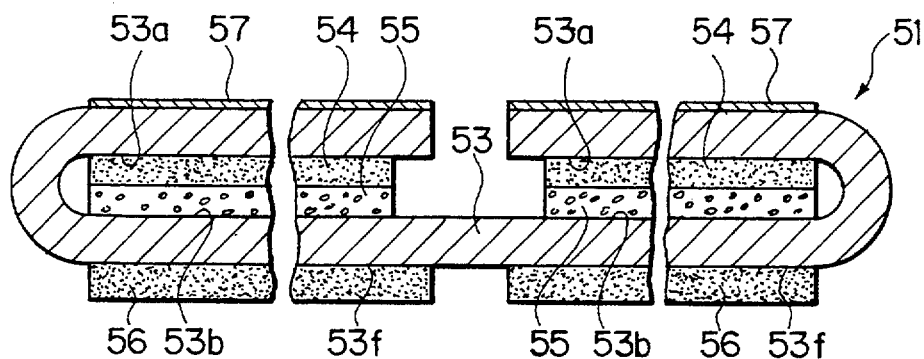
FIG. 17 is a view showing another embodiment of the pressure-sensitive tape of the present invention.

In FIG. 17 is shown one obtained by folding both of a near-one-end part and a near-other-end part in a tape substrate 53 toward the central part of the tape substrate 53 in a manner such that they become faced to each other, forming a second pressure-sensitive adhesive layer 54 and a first pressure-sensitive adhesive layer 55 on both inner surfaces 53a and 53b, respectively, in both of the left and right folded parts, and on the other hand, forming third pressure-sensitive adhesive layers 56 on outer surfaces 53f and 53f which are among the outer surfaces of both folded parts and are positioned near the central part of the tape substrate 53. In this case, both third pressure-sensitive adhesive layers 56 and 56 may be connected as shown by the alternate long and short dash line.

Figure 18:
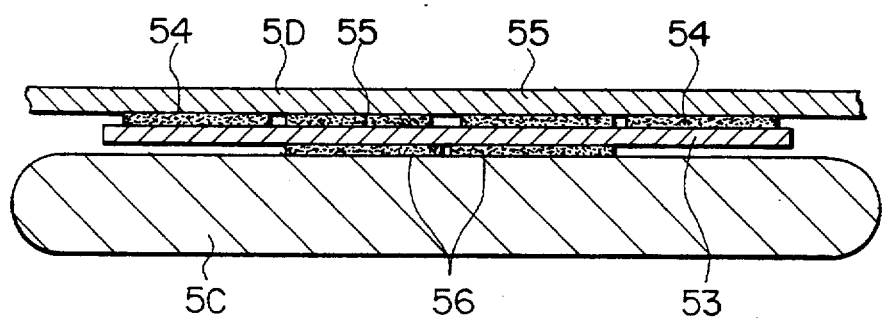
FIG. 18 is a view showing the pressure-sensitive tape of FIG. 17 which is in a state of being used.

The pressure-sensitive tape 51 shown in FIG. 17 is used in a manner such that, as shown in FIG. 18, the pressure-sensitive tape 51 is applied to one member 5C through the third pressure-sensitive adhesive layer 56, the second pressure-sensitive adhesive layers 54 in both of the left and right folded parts are separated from the first pressure-sensitive adhesive layers 55 to unfold the tape substrate 53 to make it in the shape of a single sheet, and the paired second and first pressure-sensitive adhesive layers 54 and 55 in each of the left and right parts are bonded to another member 5D. For example, it is suitable as a fixing tape for sanitary napkins.

Figure 19:
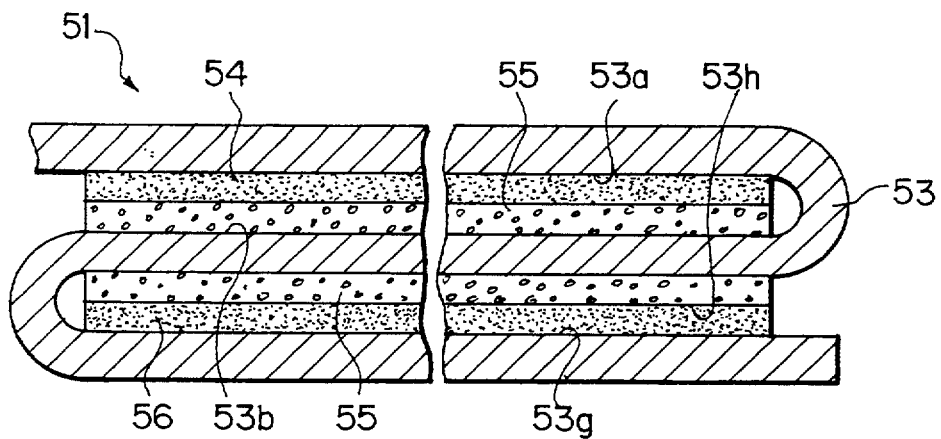
FIG. 19 is a view showing another embodiment of the pressure-sensitive tape of the present invention.

In FIG. 19 is shown one obtained by partly folding a tape substrate 53 in a manner such that parts of a near-one-end part of the substrate come to face to each other, forming a second pressure-sensitive adhesive layer 54 and a first pressure-sensitive adhesive layer 55 on both inner surfaces 53a and 53b of the faced parts in the near-one-end part, on the other hand, folding a near-other-end part of the tape substrate 53 in a direction opposite, in terms of upward and downward direction, to the direction of the folding of the above near-one-end part, and forming a third pressure-sensitive adhesive layer 56 on one surface 53g of both inner surfaces of the opposed parts in the near-other-end part and a first pressure-sensitive adhesive layer 55 on the other surface 53h.

In the present invention, it is a matter of course that the combination of the compositions of the first pressure-sensitive adhesive layer and the second pressure-sensitive adhesive layer, which enables these pressure-sensitive adhesive layers to be freely separated, is not limited to the above-described examples and various combinations can be adopted.

POSSIBILITY OF INDUSTRIAL APPLICATION

As described above, the double-side pressure-sensitive tape of the first embodiment of the present invention has the effect that it is free from the necessity of use of a release paper, because the pressure-sensitive adhesive layers, even when laid on or beneath the other, can be easily separated at their interface without causing the pressure-sensitive adhesives to be bonded and fixed to each other, and it is suitable for use as a fixing tape for diapers, napkins, and the like.

Further, in the pressure-sensitive tape of the second embodiment of the present invention, since pressure-sensitive adhesive layers are formed on two surfaces of the tape substrate which are faced to each other, the area in which the tape substrate is bonded to other member can be doubled as compared with conventional ones even when the substrate has the same area as conventional ones.

Therefore, according to the second embodiment of the present invention, since the area in which the tape substrate is bonded to other member can be doubled without increasing the area of the tape substrate, it has the effect to significantly improve fixing strength without increasing the production cost.

What is claimed is:

1. A double-sided pressure-sensitive adhesive tape having a double-folded tape substrate of sheet material, comprising a first pressure-sensitive adhesive layer formed on one surface in each fold of said double-folded tape substrate, and a second pressure-sensitive adhesive layer formed on the opposite surface from said first pressure-sensitive adhesive layer in each fold of said double-folded tape substrate, wherein said second pressure-sensitive adhesive layer and said first pressure-sensitive adhesive layer are made of different pressure-sensitive adhesive compositions and are separably bonded to each other, and wherein a third pressure-sensitive adhesive layer is formed on a surface of said double-folded tape substrate on the outside of each fold of said double-folded tape substrate, wherein said first pressure sensitive adhesive layer comprises a composition of a blend of 100 parts by weight of an acrylic or rubber-based pressure sensitive adhesive composition having from 0.01 to 30 parts by weight of a silicone polymer.

2. A double-sided pressure-sensitive adhesive tape having a double-folded tape substrate of sheet material, comprising
 a first pressure-sensitive adhesive layer formed on one surface in each fold of said double-folded tape substrate,
 a second pressure-sensitive adhesive layer formed on the opposite surface from said first pressure-sensitive adhesive layer in a fold of said double-folded tape substrate, and
 a third pressure-sensitive adhesive layer is formed on the opposite surface from said first pressure-sensitive adhesive layer in another different fold of said double-folded tape substrate,
wherein said second pressure-sensitive adhesive layer and said third pressure-sensitive adhesive layer are made of different pressure-sensitive adhesive compositions than said first pressure-sensitive adhesive layer, and wherein the pressure-sensitive adhesive layers in each fold of said double-folded tape substrate are separably bonded to each other, wherein said first pressure sensitive adhesive layer comprises a composition of a blend of 100 parts by weight of an acrylic or rubber-based pressure sensitive adhesive composition having from 0.01 to 30 parts by weight of a silicone polymer.

* * * * *